United States Patent [19]

Burton

[11] Patent Number: 4,662,890

[45] Date of Patent: May 5, 1987

[54] TUBULAR MEDICAL PROSTHESIS

[75] Inventor: Thomas A. Burton, Rochester, Minn.

[73] Assignee: Waters Instruments, Inc., Rochester, Minn.

[21] Appl. No.: 658,680

[22] Filed: Oct. 9, 1984

[51] Int. Cl.[4] .............................................. A61F 2/54
[52] U.S. Cl. ...................... 623/66; 604/328; 604/276; 604/277; 128/1 R
[58] Field of Search ...................... 128/1 R, DIG. 25; 604/327, 328, 338, 339, 276, 277; 3/1

[56] References Cited

U.S. PATENT DOCUMENTS

| | | | |
|---|---|---|---|
| 3,828,782 | 8/1974 | Polin | 604/328 X |
| 4,067,335 | 1/1978 | Silvanov | 604/328 |
| 4,183,357 | 1/1980 | Bentley et al. | 604/328 X |

Primary Examiner—Richard J. Apley
Assistant Examiner—Alan W. Cannon
Attorney, Agent, or Firm—James R. Haller

[57] ABSTRACT

A tubular prosthesis comprising a tube having an inner end securable deeply within an outwardly-open body opening and an outer end affixed to a mounting plate. The outer tube end may be everted upon a circumferentially positioned rigid ring, the thus enlarged tube end bearing against an orifice formed in the mounting plate. A forwardly-facing bore formed in the plate coaxial with the orifice is sized to snugly receive the enlarged end of the tube. A disclosed embodiment utilizes a pair of tubes coaxially joined within the bore of the plate, one tube end being everted upon a rigid supporting ring and the everted end being received within the open adjacent end of the outermost tube. The plate may have securing means for holding the outer tube in a sealed, folded back orientation.

11 Claims, 9 Drawing Figures

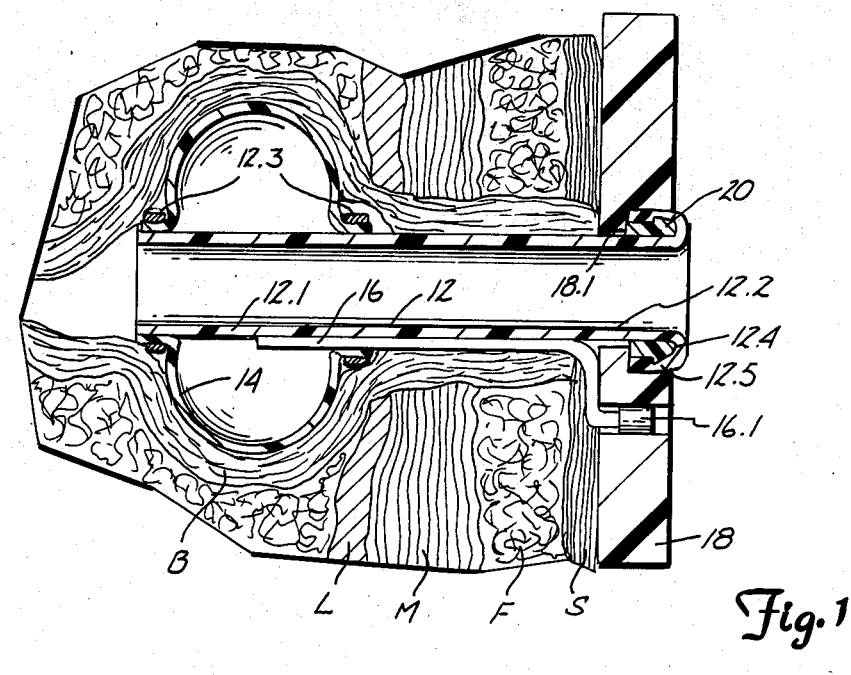
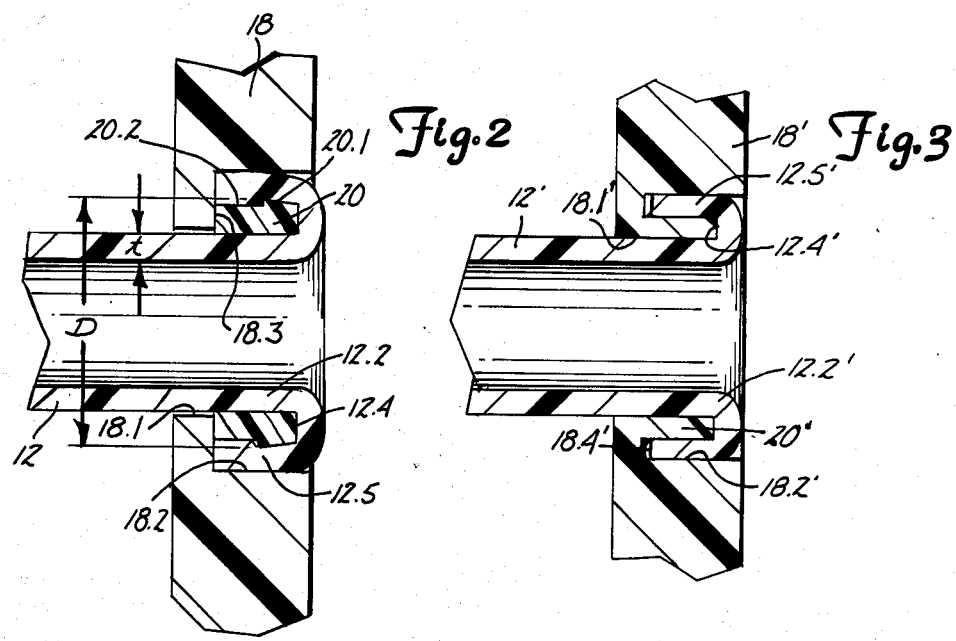

TUBULAR MEDICAL PROSTHESIS

TECHNICAL FIELD

This invention relates to the field of medical prosthetic devices and particularly to tubular devices for use by patients having surgically formed, functional body openings.

BACKGROUND ART

Patients with surgical ostomy operations commonly are provided with externally worn ostomy bags. An ostomy bag has an opening adhesively sealed to the skin of the patient about the ostomy stoma. The bags must be periodically removed and emptied, and the adhesive seal must be maintained waterproof and air-tight to prevent the escape of embarrassing odors. The skin area to which the adhesive is applied often becomes irritated, and the problem may be compounded by contact of the irritated skin with bowel contents and may lead to serious and even life-threatening infections.

Similarly, patients who have undergone certain types of throat surgery cannot ingest food normally through the esophagus. Instead, a patient may be provided with a gastric feeding tube which extends through a surgical incision from the stomach outwardly through the skin, and through which food, generally in liquid or semi-liquid form, is added directly to the stomach. Prostheses of this type must remain securely in place, and must sealingly engage the stomach and the exterior skin of the patient overlying the stomach so as to prevent the escape of stomach contents into the abdominal or thoracic cavity or permit the stomach contents to contact the wound through which the gastric feeding tube passes. Hence, problems are presented that are similar to those of ostomy patients.

My U.S. Pat. No. 4,381,765 discloses a medical prosthesis that includes a drainage tube, the inner end of which is secured to the stoma of a patient deep to the fascia, and the outer end portion of which is releasably sealed. By securing the inner end portion of the drainage tube deep to the fascia, the drainage tube may be put under tension by securing its forward or outer end to a plate which bears against the patient's skin. One means for attaching the forward end of the tube to the plate is shown in my U.S. Pat. No. 4,381,765, the tube extending through the plate and being folded upon itself. It is desirable, however, to be able to terminate the drainage tube at the plate, the drainage tube being maintained in tension between its attachment to the plate and its inner securement deep to the fascia (with ostomy patients), and within the stomach (for gastric feeding patients).

SUMMARY OF THE INVENTION

The invention provides a tubular prosthesis comprising a tube having a rearward, inner end and a forward, outer end, and means for securing the inner end of the tube deep within a surgically formed body opening, e.g.; deep to the fascia of an ostomy patient or within the stomach of a patient requiring gastric feeding or other treatment. A mounting plate is provided with an orifice through which forwardly passes the outer tube end, the latter being everted to form an annular crease. Rigid ring means are received in the crease, the diameter of the everted tube end containing the ring being greater than the smallest diameter of the plate orifice to prevent the thus enlarged, everted tube end from being drawn rearwardly through the plate orifice. In this manner, the outer or forward end of the tube is attached securely to the plate, and tension in the tube between the inner securing means and the plate restrains the tube securely in place. Desirably, the plate has a forwardly open, enlarged bore coaxial with the oriface and sized to snuggly receive the everted tube end containing the ring, the everted tube end thus being squeezed or pinched between confronting walls of the ring and bore to hold the tube to the plate.

The prosthesis may include a pair of tubes such as drainage tubes, desirably of different wall thicknesses and having adjacent ends coaxially joined to one another at the plate, one tube having an everted, ring-containing end portion received snuggly within the adjacent end portion of the other tube. The plate is provided with a forwardly open bore sized to snuggly receive the adjacent tube ends and to squeeze or pinch the same between it and the ring to hold both tubes to the plate.

DESCRIPTION OF THE DRAWING

FIG. 1 is a broken-away, cross-sectional view of a prosthesis of the invention, showing the same secured within the stoma of an ostomy patient deep to the fascia;

FIG. 2 is an enlarged, broken-away, cross-sectional view of a portion of FIG. 1 showing in greater detail the attachment of the tubular element to a supporting plate;

FIG. 3 is a view similar to that of FIG. 2 but showing a modified embodiment;

BEST MODE FOR CARRYING OUT THE INVENTION

Figure 4:
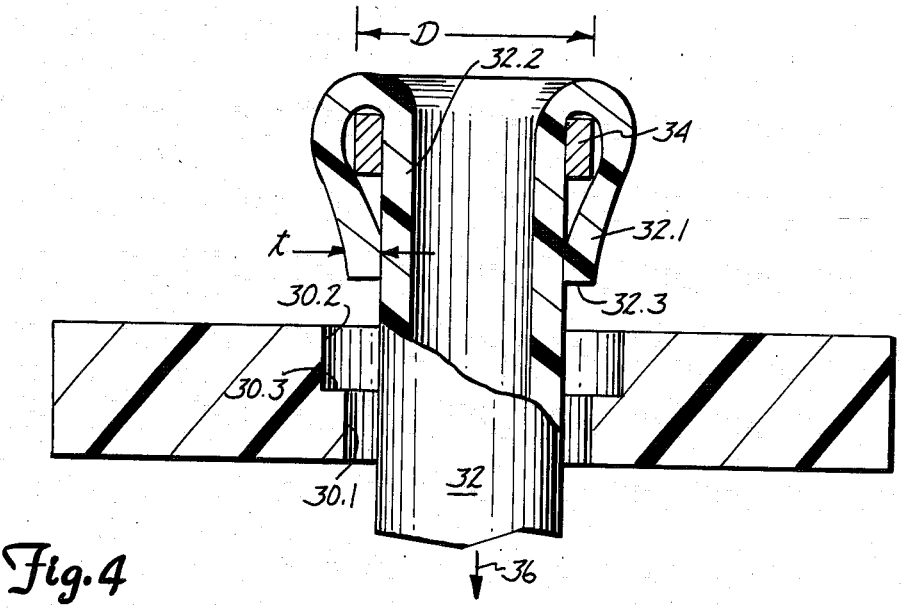
FIG. 4 is an exploded view similar to that of FIG. 2 but showing another modification of the invention.

FIG. 1 shows a device of the invention secured within the stoma of an ostomy patient. It will be understood that this device may as well be secured within other body openings. For ease of understandings, the bowel of a patient is designated "B", the fascia as "L", the muscle layer as "M", a fat layer as "F" and the skin as "S".

An ostomy drainage tube is shown generally at (12), the tube having an inner end (12.1) that is insertable into the stoma of a patient, and an outer end portion (12.2) which protrudes from a surgical opening formed in the patient's skin "S" where the bowel end emerges. The inner or rearward portion (12.1) of the tube is provided with an inflatable, circumferential balloon structure shown generally as (14), this structure comprising an annular film of resilient, inflatable material that is circumferentially attached to the drainage tube (12) at two axially spaced locations. An inflation tube, shown at (16), has one end carried within the balloon-like structure (14), its outer end passing through the opening in the skin "S" and terminating in a plug (16.1). The plug may consist simply of a small cylinder of silicone rubber or the like having a pierced hole through its thickness, the cylinder being carried within the outer end of the inflation tube. The pierced hole through the cylindrical plug may be opened by inserting in it a blunt-nosed hypodermic needle to enable the balloon-like structure (14) to be inflated with saline or other fluid. Circumferential bands (12.3) secure ends of the film forming the balloon structure (14) to the drainage tube. A similar structure is shown in my U.S. Pat. No. 4,381,765, the teachings of which are incorporated herein by reference.

As will be seen from FIG. 1, when the balloon structure (14) is inflated as shown, it dialates the bowel "B" such that when the tube (12) is pulled forwardly or outwardly of the stoma, the dialated bowel "B" bears forwardly against the fascia "L" and thus secures the drainage tube (12) in place.

A mounting plate is shown at (18) in FIG. 1 and, as shown, may bear rearwardly against the patient's skin "S". The mounting plate (18) may be generally disc-shaped, and is provided with a central orifice (18.1) through which passes the outer end portion (12.2) of the drainage tube. The orifice (18.1) will be described herein as having a circular cross-section, although it will be understood that other near circular cross-sections can be utilized as well.

The forward end (12.2) of the drainage tube is everted upon itself; that is, it is turned inside out, providing an annular crease designated generally as (12.4). The axial length of the everted portion desirably is less than twice the outer diameter of the tube, and desirably ranges from about one-third of the tube diameter to about one and a half of the tube diameter. Carried within the annular crease (12.4) is a rigid ring (20), the latter having an axial dimension ranging from about one-third to about one and one-third of the length of the everted tubular portion (12.5). Desirably, the axial dimension of the ring is approximately the same as the actual axial length of the everted tubular portion. If desired, the ring may have an exterior, annular rib such as that shown at (20.1) in FIG. 2 for the purpose of more securely engaging the everted end portion (12.5) of the drainage tube. The circumferential rib (20.1) typified in FIG. 2 has a sawtooth configuration, but other configurations may also be used. Alternatively, or in addition, the outer surface (20.2) of the ring may be roughened so as to increase friction between it and the everted tube end.

A bore (18.2) (FIG. 2) is formed in the plate (18) coaxially of the orifice (18.1) and opens outwardly forwardly of the plate (18). The bore (18.2) terminates inwardly of the disc in an annular, forwardly facing shoulder (18.3) which may be tapered if desired. The minimum diameter of the bore (18.2) of the embodiment of FIG. 2 is approximately equal to the maximum outer diameter of the ring plus twice the wall thickness of the everted tube portion. That is, the minimum bore diameter is equal to or preferably slightly less than the value D+2t wherein D is the outer diameter of the ring and t is the wall thickness of the everted tube. Of course, the diameter of the plate orifice is less than this value. Thus, when the everted end portion of the tube with its enclosed annular ring are properly positioned in the plate (18), the ring (20) or the everted tube end or both abuts the shoulder (18.3) and the outer walls of the everted tube portion are snugly received in the bore (18.2), the latter forcing the everted tube portion into contact with the outer surface of the ring and the confronting surfaces of the ring and bore serving to pinch or squeeze the tubing walls to secure the tube to the plate.

In use, the inner end of the tube (12) of the invention is inserted into the stoma, the balloon structure is inflated, and the protruding tubular portion is cut to the correct length for the use of a particular patient. The forward end of the tube is then passed forwardly through the orifice (18.1). Over the protruding end of the tube is placed the ring (20), following which the tube end is manually everted as shown in FIG. 2. By pulling rearwardly on the tube (12), the thus enlarged tube end is drawn into contact with the shoulder (18.3) of the plate, the everted tube end thus being held firmly in place against rearward movement with respect to the plate. The inner end (12.1) of the tube is then reinserted into the body opening (e.g., the stoma of an ostomy patient), the plate is pushed inwardly against the skin and the balloon structure (14) is suitably inflated. When inward pressure against the plate is released, the body tissue between the plate and the balloon structure (14) maintains the tube (12) therebetween in tension and thus securely holds the tube (12) to the body opening.

In the modification of FIG. 3, in which similar numerals, primed, identify similar structure to that shown in FIGS. 1 and 2, the ring (20') is shown as being formed integrally with the plate (18'). The confronting surfaces of the ring (20') and enlarged bore (18.2') define an annular slot (18.4') that opens forwardly from the plate (18). The slot is coaxial with the bore (18.1') and has a width approximately equal to the wall thickness of the everted tubular portion (12.5'). In this embodiment, the tube end (12.2') is brought forwardly through the orifice (18.1'), is then everted as shown in FIG. 3, and is drawn rearwardly, the ring (20) being received in the crease formed between the confronting walls of the tube and the everted portion thereof.

As shown in the embodiments of FIGS. 2 and 3, the edges of the ring (20) which come into contact with the surface of the tube in the crease (12.4), (12.4') are quite sharp and tend to dig into the walls of the tube, preventing the tube from escaping through the bore by gradually sliding around the ring.

With reference now to FIG. 4, a plate is shown as (30) and includes an orifice (30.1) and a coaxially formed, forwardly open bore (30.2). The orifice (30.1) has a minimum diameter desirably approximately equal to the outer diameter of the tube (32) plus twice the wall thickness of the everted tube section (32.1); that is, the diameter of the aperture (30.1) desirably is not less than about "d+2t" in which d is the outer diameter of the drainage tube (32) and t is the wall thickness of the everted tubular portion (32.1).

Figure 5:
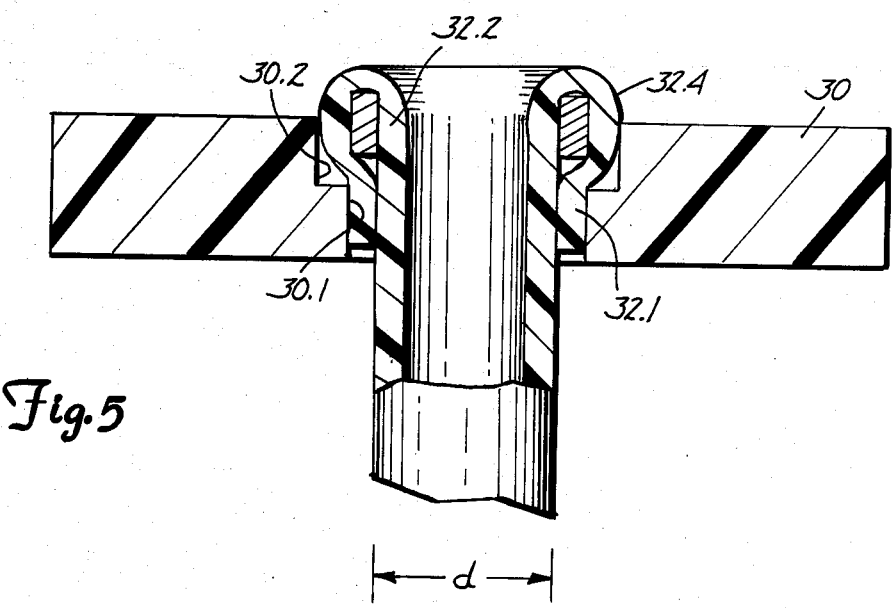
FIG. 5 is a view similar to that of FIG. 4 wherein plate and tube elements are secured one to the other.

A ring, (34), similar to the ring (20) shown in FIG. 2, is placed about the forwardly protruding end (32.2) of the drainage tube, and that end is then everted as shown in FIGS. 4 and 5. The end (32.3) of the everted portion extends well beyond the ring (34). When the everted tube end is pulled rearwardly in the direction shown by the arrow (36), the rearwardmost portion of the everted end is received within the orifice (30.1) as shown in FIG. 5. The ring is of sufficient radial thickness so as to cause the forward end of the everted tube to bulge out as shown at (32.4), the latter coming into contact with the annular shoulder (30.3) (FIG. 4) extending between the walls of the bore (30.2) and the orifice (30.1) and preventing the everted end portion of the tube from being drawn rearwardly any further. Desirably, the maximum outer diameter "D" of the ring is approximately equal to or slightly greater than the diameter of the orifice (30.1). To secure the outer end portion of the tube in place, however, it is only necessary that the outer diameter of the ring plus twice the wall thickness of the everted portion (that is, D+2t, where D and t are as defined above) are at least slightly larger than the narrowest diameter of the orifice (30.1). It is understood that the orifice (30.1) may have tapering, rearwardly converging walls.

As noted earlier, the device of the invention may be employed also for gastric feeding purposes. An incision may be made from outside the body extending into the stomach cavity. Through the incision may be inserted the rearward or inner end of the tube shown at (12) in FIG. 1, the balloon portion (14) thereof being immediately inflated and the tube being tugged outwardly so as to seal the balloon structure (14) against the inner wall of the stomach adjacent the surgical opening therein. The outer end portion of the tube passes outwardly through the skin and is secured to a mounting plate (18) in the manner described above, the mounting plate pressing inwardly upon the skin (directly, or indirectly through a gauze pad or the like) to secure the device in place.

If desired, the prosthesis of the invention can be used as a separate plug for the purpose of blocking and unblocking, for example, an ostomy opening. For use as a plug, the prosthesis is inserted and inflated as described above, the tube having an interior blockage or plug of silicone rubber or the like to prevent the passage of bowel contents therethrough. Desirably, the rearward end of the tube is plugged so as to minimize internal tube contamination. When the prosthesis is to be removed, the balloon structure is merely deflated and the prosthesis is pulled outwardly of the stoma.

It will be noted that the everted end of the tube, as shown in FIGS. 1-5, provides a smooth-walled, forwardly open mouth which can readily receive a tapered plug or other closure member.

Figure 6:
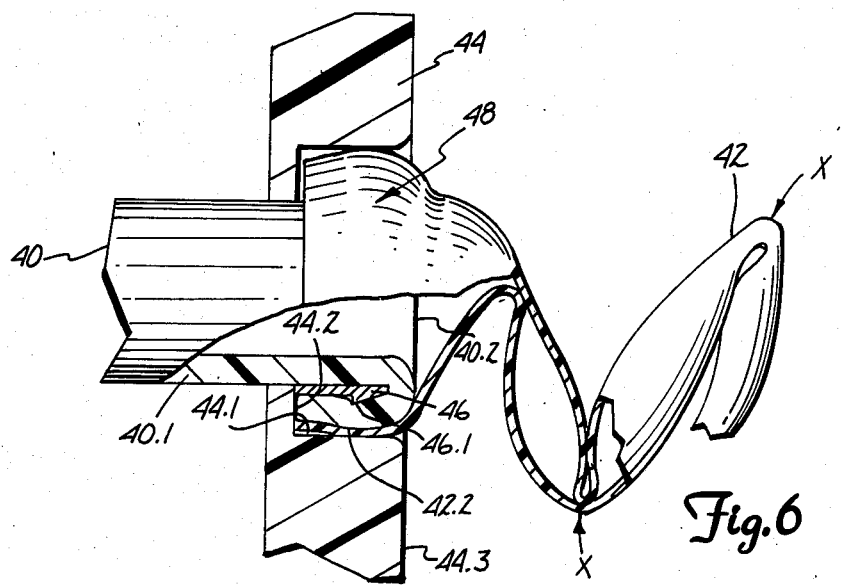
FIG. 6 is broken-away view in partial cross-section of another modified embodiment of the invention.
Figure 7:
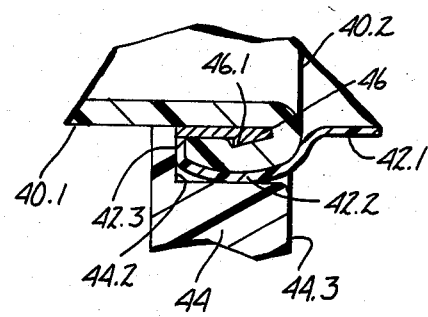
FIG. 7 is a view similar to that of FIG. 6 but showing a further modification thereof.

Referring now to FIG. 6, the prosthesis of the invention may include a pair of tubes as shown at (40) and (42) in FIG. 6, these tubes having adjacent ends (40.1), (42.1), joined to one another and to the plate (44). The tube end (40.1), as shown in FIG. 6, is everted to form a circumferential crease, and a ring (46) having an outer sharp circumferential bead (46.1) is received in the crease, all in the same manner as described above with respect to the embodiment of FIGS. 1 and 2. However, the adjacent end (42.1) of the other tube is resiliently opened and receives within it the everted end of the tube (40) to form an enlarged or bulging structure designated (48). This structure, in turn, is received within the bore (44.1) such that the everted end portion of the tube (40) and the overlying portion (42.2) of the tube (42) are pinched or squeezed between the confronting surfaces of the ring (46) and circumferential wall of the bore (44.1). Accordingly, in this embodiment, the diameter of the bore (44.1) is not greater than the largest outer diameter of the ring (46) plus twice the sum of the wall thicknesses of the two tubes (40), (42). If desired, the end (42.3) of the tube (42) may substantially completely encompass the end of the everted tube portion as shown in FIG. 7, the end (42.3), coming into contact with the shoulder (44.2) of the plate (44).

In a preferred embodiment, the thicker walled tube (40) in the embodiment of FIG. 6 represents the drainage tube shown at (12) in FIGS. 1 and 2, the other tube (42) extending forwardly from the plate (44) (that is, outwardly from the patient). The tube (42), as depicted, may have relatively thin walls enabling the tube to collapse upon itself readily and to crease, as shown at "X" in FIGS. 6 and 8. The creases formed when the thin-walled tube (42) is bent upon itself provide a generally waterproof seal, and the seals formed by these creases are generally more secure when formed in a thin-walled tube than in a thicker walled tube such as that shown as (40). The outer surface (44.3) of the plate (44) may be provided with means holding the thin-walled section of tubing (42) in a collapsed, doubled-back orientation such as that shown in FIGS. 6 and 8; that is, the tube (42) that extends forwardly from the forward surface (44.3) of the plate bent upon the plate first in one direction and then in the other to form at least one crease "X" and preferably at least two such creases.

Figure 8:
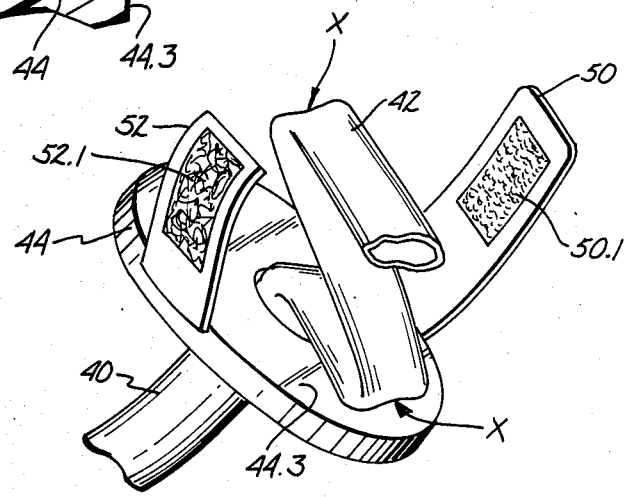
FIG. 8 is a perspective view of the device of FIG. 6.

The doubled-back portion of tubing can then be stored flatly against the forward plate surface (44.3). Means for holding the folded back tubing (42) in place is depicted in FIG. 8 as comprising a pair of flexible fabric strips (50), (52) having mating attachment surfaces (50.1), (52.1) provided with hook-and-eye fastening material such as that sold under the trademark "Velcro", or with adhesive or the like, the strips (50), (52) being folded down upon the doubled-back portion of tubing (42) and being attached to one another to hold the folded tubing in place flatly against the plate (44) to provide a flat, low-profile exterior apparatus portion that can be unobtrusively worn by a patient.

Figure 9:
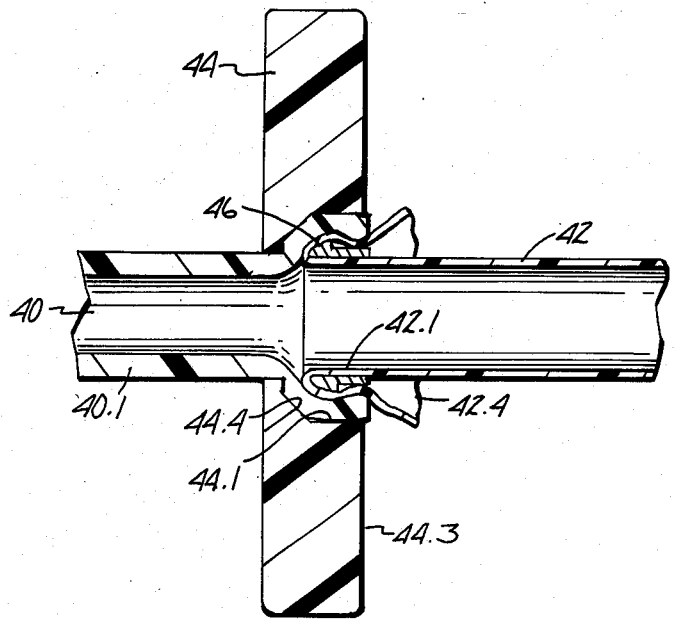
FIG. 9 is a broken-away view in cross section similar to that of FIG. 6 and showing another modification.

With reference to FIG. 9, it will be understood that the thicker and thinner walled tubing sections may be reversed if desired, the thinner walled tubing (42) being provided with the everted end over which is received the end (40.1) of the thicker walled tubing section. Also, although the everted tubing end is shown as opening forwardly (to the right in FIG. 6), the orientation of the everted tubing may be reversed. This configuration provides a secure, water-proof juncture between the tubes at the plate (44). The end of the thin-walled, outer tube (42) may be flaired as shown at (42.4). The bore (44.1) may have a rearward, inwardly tapered portion (44.4) to firmly engage the exterior wall of the tube (40).

The tubes (12), (32) and (40) shown in the various drawings are desirably made of a physiologically acceptable polymeric material; silicone rubber tubing has given good results. Such tubes may have an outer diameter of about 13 millimeters and a wall thickness of about 1.5 millimeters, but tubing dimensions may be varied as desired. The tubing is sufficiently flexible as to enable its forward end to be everted, as taught herein, by manual manipulation. Yet, the tubing desirably is sufficiently stiff as to tend to retain an open cross-section within a body opening, e.g., the stoma of an ostomy patient. The ring, shown in the drawings variously as (20) and (46), preferably is made of a metal such as aluminum or stainless steel or of other stiff and strong material. The ring is rigid so that it maintains the generally circular cross-sectional configuration of the tube end that is everted upon it. The second tube shown at (42) in FIGS. 6-8 may have an inner diameter approximately equal to the outer diameter of the thicker walled tube (40), and may have a wall thickness on the order of 0.5 millimeters. The tube (42) is very pliant and flexible, and can easily be folded into the serpentine configuration shown in FIG. 8. Again, the tube (42) also desirably is made of a physiologically acceptable silicone rubber.

While preferred embodiments of the present invention have been described, it should be understood that various changes, adaptations and modifications may be made therein without departing from the spirit of the invention and the scope of the appended claims.

What is claimed is:

1. A tubular prosthesis comprising a tube of a physiologically acceptable polymeric material having a rearward, inner end and a forward, outer end, means for securing the inner end of the tube deep within an outwardly open body opening, and a mounting plate receivable against the exterior of the skin adjacent the body opening and having an orifice through which forwardly passes the outer tube end, the latter being everted to form an annular crease, and a rigid ring received in the crease, the diameter of the everted tube end overlying the ring being greater than the diameter of the plate orifice and preventing the everted tube end overlying the ring from being drawn rearwardly through the plate orifice.

2. A tubular prosthesis comprising a tube of a physiologically acceptable polymeric material having a rearward, inner end portion and a forward, outer end portion, means for securing the inner end portion of the tube deep within an outwardly open body opening, and a mounting plate receivable against the exterior of the skin adjacent the body opening and having an orifice through which forwardly passes the outer tube end portion, the latter being everted to form an annular crease, a rigid ring received in the crease, the diameter of the everted tube end portion overlying the ring being greater than the diameter of the plate orifice, the mounting plate including a forwardly-open bore coaxial with the orifice and sized to receive the everted, ring-containing tube end portion.

3. The prosthesis of claim 2 in which the diameter of the plate orifice is less than $D+2t$ wherein $D$ is the outer diameter of the ring and $t$ is the wall thickness of the everted tube end.

4. The prosthesis of claim 3 wherein the outer diameter of the ring is greater than the diameter of the plate orifice.

5. A tubular prosthesis comprising a tube of a physiologically acceptable polymeric material having a rearward, inner end and a forward, outer end, means for securing the inner end of the tube deep within an outwardly open body opening, and a mounting plate receivable against the exterior of the skin adjacent the body opening and having an orifice through which forwardly passes the outer tube end, the mounting plate including a forwardly open bore coaxial with but larger than the orifice, the forward end of the tube being everted to form an annular crease, and a rigid ring received in the crease, the diameter of the plate orifice being less than $D+2t$ wherein $D$ is the outer diameter of the ring and $t$ is the wall thickness of the everted tube end, the bore being sized to snugly receive the everted, ring-containing tube end to thereby pinch the everted tube end between confronting walls of the ring and bore to securely hold the tube to the plate.

6. A tubular prosthesis comprising a first tube of a physiologically acceptable polymeric material having a rearward, inner end and a forward, outer end, means for securing the inner end of the first tube deep within an outwardly open body opening, a mounting plate receivable against the exterior of the skin adjacent the body opening and having an orifice through which forwardly passes the outer first tube end, a second tube of a physiologically acceptable polymeric material having an end adjacent the forward end of the first tube, one of said tube ends being everted to form an annular crease, a rigid ring received in the crease, the everted tube end being received coaxially within the adjacent open end of the other tube to form a circumferential seal between the adjacent tube ends, the mounting plate having a forwardly open bore coaxial with the orifice and sized to snugly receive the adjacent, circumferentially sealed tube ends.

7. The apparatus of claim 6 in which the bore has a diameter not greater than $D+2(t+T)$ wherein $D$ is the outer diameter of the ring, $t$ is the wall thickness of the tube having the everted end and $T$ is the wall thickness of the other tube.

8. The apparatus of claim 6 in which the diameter of the plate orifice is less than the diameter of the coaxial bore.

9. The apparatus of claim 6 in which the outer end of the first tube is provided with the everted end portion.

10. The apparatus of claim 6 including means for securing said second tube in a collapsed, folded back orientation flatly against the mounting plate with creases in said tube providing at least one waterproof seal.

11. A tubular prosthesis comprising a tube of a physiologically acceptable polymeric material having a rearward, inner end and a forward, outer end, means for securing the inner end of the tube deep within an outwardly open body opening, and a mounting plate receivable against the skin adjacent the exterior of the body opening and having an orifice through which forwardly passes the outer tube end, the latter being everted to form an annular crease, and a rigid ring received in the crease, the diameter of the everted tube end overlying the ring being greater than the diameter of the plate orifice and preventing the everted tube end overlying the ring from being drawn rearwardly through the plate orifice, the mounting plate including a forwardly-open bore coaxial with the orifice and sized to snugly receive the everted, ring-containing tube end to thereby pinch the everted tube end between confronting walls of the ring and bore to securely hold the tube to the plate.

* * * * *